United States Patent [19]

Bernard et al.

[11] 4,417,083

[45] Nov. 22, 1983

[54] PROCESS FOR THE DEHYDROCYCLIZATION OF PARAFFINS AT LOW PRESSURE

[75] Inventors: Jean-Rene Bernard, Serezin du Rhone; Michèle Breysse, Villeurbanne, both of France

[73] Assignee: Elf France, Paris, France

[21] Appl. No.: 451,753

[22] Filed: Dec. 21, 1982

Related U.S. Application Data

[63] Continuation of Ser. No. 256,087, Apr. 21, 1981, abandoned.

[30] Foreign Application Priority Data

May 9, 1980 [FR] France .................... 80 10411

[51] Int. Cl.³ .................... C10C 5/24; C10C 5/30
[52] U.S. Cl. .................... 585/419; 252/411 R; 208/140; 585/402; 585/415; 585/311
[58] Field of Search ............... 585/402, 403, 412, 415, 585/419, 311; 208/138, 137, 140; 252/411 R

[56] References Cited

U.S. PATENT DOCUMENTS

| | | | |
|---|---|---|---|
| 2,758,063 | 8/1956 | McLaren et al. | 252/411 R |
| 3,210,265 | 10/1965 | Garwood | 252/411 R |
| 3,352,941 | 11/1967 | Schoen et al. | 252/411 R |
| 3,389,191 | 6/1968 | Estes | 252/411 R |
| 3,755,486 | 8/1973 | Oishi et al. | 585/419 |
| 3,775,502 | 11/1973 | Oishi et al. | 585/419 |
| 3,878,122 | 4/1975 | Pennella | 252/411 R |
| 4,104,320 | 8/1978 | Bernard et al. | 585/419 |
| 4,304,658 | 12/1981 | Reinhard et al. | 252/411 R |
| 4,379,756 | 4/1983 | Weitz et al. | 252/411 R |

FOREIGN PATENT DOCUMENTS

| | | | |
|---|---|---|---|
| 2479707 | 10/1981 | France | 585/415 |
| 5016786 | 8/1970 | Japan | 585/419 |

*Primary Examiner*—Delbert E. Gantz
*Assistant Examiner*—A. Pal
*Attorney, Agent, or Firm*—Burgess, Ryan & Wayne

[57] ABSTRACT

A process for the production of aromatic hydrocarbons from petroleum fractions containing paraffins which comprises passing said charge in the presence of hydrogen at 400° C.–550° C. over a catalyst containing from 0.1 to 1.5% by weight of at least one metal selected from the group consisting of platinum, rhenium, iridium, tin and germanium and containing sulfur in a sulfur/metals atomic ratio of from 0 to less than 1, supported on a crystalline, aluminum silicate zeolite containing alkaline cations, said zeolite having a pore dimension larger than 6.5 Angstroms, wherein the catalysts are in fixed beds in two reactors or sets of reactors arranged in parallel and operate at a pressure on the order of from 0.5 to 8 absolute bars wherein when a reactor set ($DHC_1$) is producing aromatic hydrocarbons the other reactor set ($DHC_2$) is swept by the hydrogen produced by the first reactor set ($DHC_1$) at a temperature adequate for reactivating the catalyst, then inverting the roles of the two sets.

8 Claims, 1 Drawing Figure

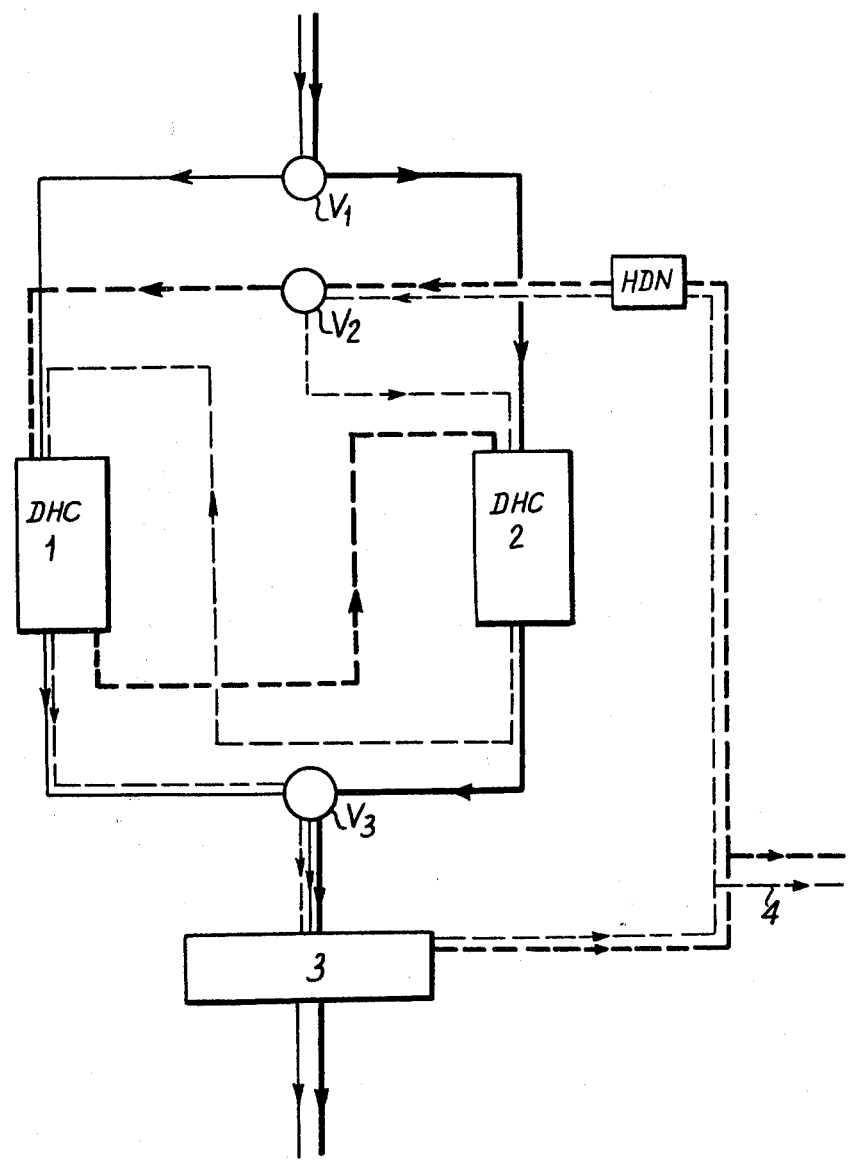

PROCESS FOR THE DEHYDROCYCLIZATION OF PARAFFINS AT LOW PRESSURE

This is a continuation of application Ser. No. 256,087, filed Apr. 21, 1981, now abandoned.

BACKGROUND OF THE INVENTION

This invention is a catalytic process for the production of aromatic hydrocarbons with high yields.

A stable catalyst capable of being regenerated by treatment with hydrogen is used at low pressure in two sets of reactors arranged in parallel, one set of reactors being used to dehydrocyclize the hydrocarbons and the other set of reactors being regenerated by the hydrogen produced by the dehydrocyclization reaction.

The customary methods for aromatization of paraffins are based on the use of catalysts comprising a noble metal on a carrier, in particular catalysts containing from 0.2 to 0.8% by weight of platinum on a carrier of chlorinated alumina at 0.2-2% by weight. To be sufficiently stable, these catalysts must operate at a relatively high pressure (on the order of 30 atm.) in the presence of a hydrogen excess (6 moles $H_2$ per mole of hydrocarbons) to limit the formation of coke. Unfortunately, the high pressure and hydrogen content thermodynamically and kinetically limit the dehydrocyclization reactions and promote the undesirable hydrocracking reactions.

An important improvement in these catalysts consisted in adding a second metal to the catalyst, which confers on the latter increased stability and the possibility of working at a lower pressure under conditions where the aromatization reactions are favored. Catalysts are now used which contain the coupled platinum-rhenium, or platinum-iridium, or platinum-tin, or platinum-germanium on the carrier of chlorinated alumina. The working pressures can be reduced to approximately 20 bars without affecting the cycle duration and with a remarkable increase in the yield of aromatic hydrocarbons and a reduction in the hydrocracking reactions.

Like the older catalysts, these catalysts are used in a fixed bed and after a cycle of a few months, they are regenerated by combustion of the coke followed by a treatment with a mixture of air and chlorinated compounds for dispersing the metals. After reduction by hydrogen, these catalysts are ready for use and have properties almost identical with those of a new catalyst.

Another important improvement in the process consisted of using catalysts in reactors with mobile beds. In the mobile bed reactors, the catalyst is continuously injected into the set of reactors where it remains for a period of time on the order of a few weeks. The catalyst is then withdrawn from the reactor, regenerated and then recycled to the reactor. All these operations are effected without stopping the production of aromatics. The reduction of the cycle to a few weeks makes it possible to lower the working pressure to about 10 atm., which has a favorable influence on the yields of aromatics and reduces the amount of hydrocracking which occurs in the process.

In all these processes, the catalysts comprised noble metals supported on chlorinated alumina. The catalysts become deactivated by formation of a coke which is a poorly hydrogenated polyaromatic species which limits the access of the hydrocarbons of the charge to the catalytically active sites. This coke can only be removed from the catalyst by combustion with small amounts of oxygen. The combustion operation is long and difficult since the combustion must be carefully controlled to avoid thermal degradation of the catalyst. The combustion operation must be preceded and followed by thorough purges to avoid explosions. For these reasons, the operation is effected as rarely as possible in spite of the advantages of a reduction of the pressure of the reaction which could be achieved by shortening the duration of the cycle.

The difficult regeneration of the fixed catalyst beds explains the advantage of using mobile beds with regeneration outside the reactors to achieve low working pressure. However, the duration of the cycle must still be equal at least to two weeks since it is not practical to circulate the catalyst too quickly through the bed thus requiring that the working pressure be not lower than 8–10 bars.

Other types of catalysts which are very effective in aromatization comprise platinum (from 0.1 to 1.5% by weight), optionally, a second metal such as rhenium, iridium, tin or germanium, and optionally sulfur, on a carrier comprising a crystalline aluminosilicate zeolite having a pore size larger than 6.5 Angstroms containing more than 90% alkaline cations. The zeolites can be the faujasites X and Y, the zeolite omega, the zeolite ZSM4 and the zeolite L. Zeolite L leads to specially interesting results in the aromatization of paraffins. Like the other catalysts, the zeolite supported catalysts become deactivated by formation of coke. However, we have unexpectedly observed that they can easily be regenerated by hydrogen, which makes it possible to shorten the duration of the regeneration considerably and to use them at low pressure with a spectacular improvement in yield, by using a new type of process.

BRIEF DESCRIPTION OF THE INVENTION

The invention comprises a process for the production of aromatic hydrocarbons from petroleum fractions containing paraffins.

The process comprises use of a catalyst containing noble metals and optionally, sulfur deposited on a crystalline zeolitic aluminosilicate having a pore size of larger than 6.5 Angstroms substituted with more than 90% alkali metal cations. The catalyst is placed in a fixed bed in two reactors or sets of reactors arranged in parallel and working at low pressure of from 0.5 to 8 absolute bars. When a set of reactors is producing aromatic hydrocarbons, the other set of reactors is being regenerated by being swept by the hydrogen produced by the first reactor or set of reactors at a temperature suitable for reactivating the catalyst. The cycle can last from 3 hours to 1 week and then the roles of the two reactors or sets are reversed.

It is also possible to use more than two reactors in parallel while distributing at the user's convenience, the number of reactors operating and the number of reactors being regenerated by hydrogen.

DETAILED DESCRIPTION OF THE INVENTION

The catalysts useful in the present invention comprise:

a carrier comprising a crystalline zeolitic aluminosilicate or a molecular sieve. It is essential for the dehydrocyclization that the molecular sieve serving as the carrier have a low acidity, no acidity, or low basicity. For this reason, the zeolite must have its cationic exchange sites contain at least 90% alkali metal cations; all other cations introduce a certain acidity either because they are multivalent and thus create acid sites or because they can be reduced or decomposed under the conditions of the catalysis reaction. The reduction or decomposition corresponds to the formation of protons on the zeolite. It is evident that the pores of the alkaline zeolite must have an opening at least equal to the dimensions of the benzene molecule. Among the zeolites that can be used are the Faujasites X and Y, the zeolite L, the zeolite omega and the zeolite ZSM4. These zeolites can be used in the form in which they are made except the last two that contain alkylammonium cations that must be replaced by alkali metal cations by the methods known to those skilled in the art such as the thermal decomposition followed by neutralization with an alkali metal base. It is likewise possible to exchange their synthesis cations for other alkali metal cations and the zeolites in question can therefore contain lithium, sodium, potassium, rubidium and/or cesium.

Among these zeolites, the preferred carrier is the zeolite L that leads to exceptional yields in aromatics from aliphatic fractions. This zeolite is synthesized under its potassium form and it can be economically used as such, but it can also contain sodium and especially rubidium or cesium.

The zeolite carrier must be formed into a suitably shaped article to make it suitable for industrial use. This shaping can be done either prior to or after the deposit of the catalytic materials such as platinum, rhenium and sulfur on the zeolite support. The shaping can be done by methods known to those skilled in the art such as by mixture with alumina or clay binders, and extrusion or molding in the shape of small balls or pellets, by the technique of making dragees or of coagulation in drops. Another technique that can be used is molding in the shape of small balls or moldings from clay such as metakaolin and conversion thereof to zeolites by appropriate techniques. The zeolites can likewise be used in the form of pellets or tablets.

The percentage of platinum is from 0.1 to 1.5% by weight. It can be introduced on the carrier by the methods described in the prior aart such as impregnation with an aqueous solution of a salt or of a platinum complex such as hexachloroplatinic acid, dinitrodiaminoplatinum or platinum tetramine chloride. It is also possible to use a deposit by ion exchange with an aqueous solution of a platinum cationic complex like platinum tetramine chloride.

The catalyst can contain from 0 to 1.5% rhenium that is introduced in the form of rhenium carbonyl $Re_2(CO)_{10}$ either by sublimation on the carrier or by impregnation with an organic solution. However, it is not necessary that the catalyst contains rhenium for the action of stabilization by hydrogen at high temperature to be effective.

The catalyst can contain iridium, or tin, or germanium in the range of 0-1.5%.

The catalyst can likewise contain small amounts of sulfur. During the stage of activation by hydrogen, the sulfur is probably reduced to the form of hydrosulfuric acid and its role then is to poison selectively the hydrogenolyzing function of the catalyst. The latter contains sulfur especially when it contains rhenium or iridium that are easily subject to hydrogenolysis, but the atomic ratio sulfur/Pt+other metals is not more than 1.

Before use, the catalyst must be reduced by the hydrogen at a temperature between 300° and 750° C., preferably from 550° to 750° C., the effect of which is to stabilize the catalyst.

FIG. 1 is a diagrammatic illustration of the process.

The process functions in two alternate periods, period 1 and period 2. In the FIGURE, the progress of the hydrocarbons (charge or product) is shown in solid lines; the progress of the hydrogen is shown in broken lines. The lines are thin for period 1 and thick for period 2. During period 1, the charge of hydrocarbons is directed by means of a three-way valve V1 the dehydrocyclization reactor DHC 1 containing the catalyst. It is mixed with the recycled hydrogen prior to entering the reactive section. The reactor DHC 1, just like DHC 2, can comprise a set of at least 1 to 4 reactors with intermediate reheating so as to compensate for the endothermy of the reaction, as it was known in the prior art. At the exit from the reactor DHC 1, the effluents (aromatics, non-converted charge and hydrogen) are directed by a three-way valve V3 to a separator 3. Due to the low working pressure, it is necessary to effect the separation of the hydrogen from the hydrocarbons under conditions other than a simple condensation of hydrocarbons at room temperature. In fact, the hydrogen must be of a purity of more than 85% by volume to be recycled in the reactors. The separation of the hydrogen and of the hydrocarburized products can be made by the means known to those skilled in the art such as the cooling to a low temperature or compression and expansion of the mixture. The liquid aromatic hydrocarbons are thus collected and separated from the hydrogen.

The hydrogen which is purified to more than 85% is purged at 4 from the flow corresponding to the net production of hydrogen of the process. The rest can be conveyed to a small hydrogenation reactor HDN (optional). This reactor serves to hydrogenate traces of olefins contained in the hydrogen, which olefins can accelerate deactivation of the catalyst. The hydrogen is then conveyed by the 3-way valve V2 to the set of reactors DHC 2, the effect of which is to regenerate the catalyst in DHC 2. The hydrogen is then recycled from reactor DHC 2 to reactor DHC 1 to ensure the stability of the catalyst in DHC 1.

When the catalyst in DHC 1 must be regenerated, the reactor DHC 2 becomes the dehydrocyclization reactor and the reactor DHC 1 is regenerated by the hydrogen from DHC 2.

Quite evidently, the necessary furnaces and exchangers have not been shown in this diagram in order to preserve clarity.

This process is shown exclusively by way of illustration; the process may also be carried out in three or four groups of reactors working in accordance with the same diagram. Certain reactors are in operation and others are regenerated according to whether the user prefers to minimize the expenses of purchase of the catalyst or investment in reactors.

The working conditions of the reactive section are the following:

The absolute pressure is from 0.5 to 8 absolute bars at the exit of the reactor, preferably from 0.5 to 3 bars. The pressure at the inlet of the reactor is higher due to the loss of pressure which occurs in passing through the catalyst bed. Because of the low pressure, the yield of aromatics can be substantially increased while minimizing hydrocracking. A Pt-Re catalyst on a KL zeolite produces from 35 to 38% benzene from a C$_6$ fraction at 9 absolute bars and 500° C. The same catalyst produces from 80 to 88% by weight benzene if used at atmospheric pressure at 460° C. In the same way, the yield of products of hydrocracking (of methane or pentane) is from 20% to 6% by weight.

The molar ratio of hydrogen to the hydrocarbons between reactors is from 0 and 30. The reaction temperature is from 400° to 550° C. The volume of liquid charge injected by apparent volume of catalyst per hour is between 0.2 and 10 h$^{-1}$. The duration of the period between regeneration is from about 3 hours to 7 days. It is important not to lengthen the duration of the dehydrocyclization period too much even if the catalyst is not extensively deactivated, since the coke thus formed becomes increasingly resistant to regeneration by hydrogen. The preferred maximum duration of the dehydrocyclization period is about 4 days.

The conditions of the reactivation or regeneration are the following:

The pressure is the same as, or slighly above, that of the dehydrocyclization reaction zone. The temperature of the catalyst to be reactivated is from 400° to 750° C. The reactivated hydrogen coming from the separation zone has a purity of more than 85% by volume and its flow is preferably the same as that of the hydrogen recycled in the reaction zone.

The reactivation can last the same length of time as the reaction period. Despite these periodical reactivations, small amounts of coke resistant to reactivation by hydrogen gradually accumulate in the catalyst. This coke must be eliminated by the classical methods of oxidizing regeneration known in the prior art but this is not inconvenient, since the oxidizing regeneration need only be done after several months of operation of the process.

The process of the invention can be used for the production of reformates constituting excellent carbureting bases and for the production of aromatic fractions for use in petroleum chemistry. The petroleum charges are desulphurized essences of distillation of the raw petroleum, the initial point of which is from 50° to 120° C. and the final point, from 70° to 240° C.

A 50°–80° C. fraction charge contains essentially hydrocarbons with 6 carbon atoms and produces essentially benzene. A 60°–100° C. fraction produces a mixture of benzene and toluene. Finally, an 80°–180° C. fraction produces in excellent yield, a reformate with a good octane index.

This invention will be better understood in light of the examples that follow which are not limiting.

EXAMPLE 1

20 g of catalyst containing 0.9% platinum deposited on zeolite L exchanged by potassium cations were placed in a reactor, then reduced by a hydrogen current at 600° C. for 7 hours. The catalyst was tested in the dehydrocyclization of n-hexane to benzene under the following conditions: atmospheric pressure-volume of liquid n-hexane injected per volume of catalyst per hour (VVH) 2 h$^{-1}$. Molar ratio of hydrogen to hydrocarbon 8. Reaction temperature 460° C. Under these conditions, the yield of benzene remains stable for 12 hours at 88% by weight while the yield in hydrocracking products (from C$_1$ to C$_5$) is 3.5%.

EXAMPLE 2

After 12 hours of work of the catalyst of Example 1, the charge of n-hexane is stopped and the hydrogen is allowed to sweep the catalyst at 460° C. for 12 hours. After this period of time, the charge of n-hexane is reintroduced at 460° C. The yield of benzene is 88.4%. After 6 hours of functioning, the reaction temperature is lowered to 440° C., which makes the yield of aromatics fall to 77.8%. 6 hours later at 440° C., the yield is 74.5%, which shows that the catalyst has become slightly deactivated.

EXAMPLE 3

The catalyst of Example 2 is kept in the reactor. The charge of n-hexane is stopped and hydrogen is allowed to sweep the catalyst for 12 hours at 460° C. The charge of n-hexane is then reintroduced at 460° C. for 6 hours. The yield of benzene is 88.7%. The temperature is then reduced to 440° C. and the yield is lowered to 77.8%, then to 73.8% after 6 hours at 440° C. This shows that the catalyst has been totally reactivated by the hydrogen and that it then becomes slightly deactivated with use.

EXAMPLE 4

A period identical with that of Example 3 is effected. At 460° C., the yield of benzene is 86.5%. After 6 hours, the temperature is reduced to 440° C. The yield drops to 78.7% then to 74.5% after 6 hours at 440° C.

Examples 1 to 4 show that the slight deactivation of the catalyst obtained for 12 hours is entirely capable of being regenerated by treatment with hydrogen.

EXAMPLE 5

There is used a catalyst containing 1% platinum and 0.67% rhenium deposited on a zeolite L compensated by potassium cations. This catalyst is reduced by the hydrogen at 600° C.

Under the conditions of Example 1, there is obtained a stable benzene yield of 88.5% with 5% C$_1$–C$_5$ during 24 hours. The catalyst is made alternatively to undergo 20 periods of 24 hours of reaction at 460° C. and 20 periods of 24 hours of reactivation by hydrogen at 460° C. At the twentieth period of reaction, the benzene yield is 86.2% with 3.1% C$_1$–C$_5$.

This example shows that the platinum-rhenium catalysts are also susceptible to being reactivated by hydrogen and that they can undergo a great number of reaction periods without substantial deactivation.

EXAMPLE 6

The catalyst of Example 1 is reduced by a hydrogen current at 600° C. for 10 hours under 3 absolute bars. It is then tested in dehydrocyclization of the n-hexane to benzene under the following conditions: absolute pressure 3 bars, VVH 3 h$^{-1}$, molar ratio of hydrogen to hydrocarbon 8, reaction temperature 525° C. There is obtained a yield of 81.3% of benzene with 15% C$_1$–C$_5$ for 48 hours. The catalyst is alternatively made to undergo 5 periods of 48 hours of reaction at 525° C. and 4 periods of reactivation by hydrogen at 525° C. At the fifth period of reaction, the benzene yield is 80.5% with 12.1% C$_1$–C$_5$.

What we claim is:

1. A process for the production of aromatic hydrocarbons from petroleum fractions containing paraffins which comprises passing said petroleum fractions, in the presence of hydrogen, at 400° C.–550° C. at a pressure of from about 0.5 to 8 bars absolute, over a catalyst containing from 0.1 to 1.5% by weight of at least one metal selected from the group consisting of platinum, rhenium, iridium, tin and germanium, and containing sulfur in an atomic sulfur/metals ratio of from 0 to less than 1, supported on a crystalline, zeolitic aluminosilicate compensated by alkali metal cations, having a pore dimension larger than 6.5 Angstroms, said catalyst being in a fixed bed in two reactor sets arranged in parallel in a manner such that when a set of reactors (DHC$_1$) is producing aromatic hydrocarbons, the other set of reactors (DHC$_2$) is being regenerated by contact with the hydrogen from the first set of reactors (DHC$_1$) at a temperature sufficient for reactivating the catalyst, and reversing the operation of the reactors.

2. A process according to claim 1, wherein the catalyst is activated prior to reaction by reduction with hydrogen at a temperature of from 550° C. to 750° C. for a period of 1 hour to 7 days.

3. A process according to claim 1 or 2, wherein there is included a cycle of two periods comprising:
(1) a first period in which the hydrocarbon charge mixed with recycled hydrogen is introduced into a first reactor for dehydrocyclization (DHC$_1$); (b) conveying the effluent from the reaction to a separator from which the aromatic products are separated from the hydrogen to provide a hydrogen stream containing at least 85% hydrogen by volume; (c) passing the hydrogen stream to the second set of reactors to regenerate the catalyst, and (d) passing the hydrogen from the second reactor to the recycled hydrogen to the first reactor;
(2) a second period in which the roles of the reactors are inverted and reactor (DHC$_2$) acts as the producer of aromatic hydrocarbons while the catalyst in reactor (DHC$_1$) is regenerated by the hydrogen effluent from (DHC$_2$).

4. A process accordng to claim 1 or 2, wherein the molar hydrogen/hydrocarbons ratio at the entrance of the reactor ranges from 0 to 30, the volume charge measured as a liquid, injected per apparent volume of catalyst per hour is from between 0.2 h$^{-1}$ and 10 h$^{-1}$, the absolute pressure in the reactive zone is from 0.5 to 8 bars and the temperature of reactivation by the hydrogen, pure in at least 85% by volume, ranges from 400° C. to 750° C.

5. A process according to claim 1 or 2, wherein the duration of a cycle ranges from about 3 hours to 7 days.

6. The process according to claim 5 wherein the cycle is less than 4 days.

7. A process for reactivation of a dehydrocyclization catalyst containing from about 0.1 to 1.5% by weight of at least one metal selected from the group consisting of platinum, rhenium, iridium, tin and germanium, and containing sulfur in an atomic sulfur/metal ratio of from 0 to less than 1, supported on a crystalline, zeolitic aluminosilicate compensated by alkali metal cations, having a pore dimension larger than 6.5 angstroms, said catalyst having been deactivated by the dehydrocyclization of a paraffin containing petroleum fraction in the presence of hydrogen to form aromatic hydrocarbons said process consisting essentially of: contacting the deactivated catalyst with hydrogen at a temperature of from about 400° C. to 750° C. for a period of from about 1 hour to 7 days.

8. The process of claim 7, wherein the paraffin containing hydrocarbon and hydrogen are brought into contact with the catalyst, to form aromatic hydrocarbons, at a temperature of from about 400° C. to 550° C.

* * * * *